(12) United States Patent
Akagawa

(10) Patent No.: US 8,351,816 B2
(45) Date of Patent: Jan. 8, 2013

(54) ION GENERATING UNIT WITH ION GENERATING FUNCTION AND IMAGE FORMING APPARATUS PROVIDED THEREWITH

(75) Inventor: Yuhi Akagawa, Osaka (JP)

(73) Assignee: Sharp Kabushiki Kaisha, Osaka (JP)

( * ) Notice: Subject to any disclaimer, the term of this patent is extended or adjusted under 35 U.S.C. 154(b) by 118 days.

(21) Appl. No.: 12/943,438

(22) Filed: Nov. 10, 2010

(65) Prior Publication Data

US 2011/0116828 A1   May 19, 2011

(30) Foreign Application Priority Data

Nov. 18, 2009   (JP) ................................. 2009-262987

(51) Int. Cl.
  *G03G 21/20*   (2006.01)
  *G03G 15/00*   (2006.01)
(52) U.S. Cl. ......................................... 399/93; 399/107
(58) Field of Classification Search ........................ None
See application file for complete search history.

(56) References Cited

U.S. PATENT DOCUMENTS

| 4,050,802 | A  | * | 9/1977  | Tanaka et al. .................... 399/93 |
| 2007/0230995 | A1 |   | 10/2007 | Yokota et al. |
| 2008/0219695 | A1 | * | 9/2008  | Doshohda et al. .............. 399/93 |
| 2011/0255895 | A1 | * | 10/2011 | Kim et al. ....................... 399/92 |

FOREIGN PATENT DOCUMENTS

| JP | 10-161491   | 6/1998  |
| JP | 2004-233618 | 8/2004  |
| JP | 2005-004144 | 1/2005  |
| JP | 2007-271660 | 10/2007 |
| JP | 2008-250289 | 10/2008 |

* cited by examiner

*Primary Examiner* — David Gray
*Assistant Examiner* — Sevan A Aydin
(74) *Attorney, Agent, or Firm* — Nixon & Vanderhye, P.C.

(57) ABSTRACT

An ion generating unit comprises a duct, an ion generating device, a mounting plate and a fan. The duct is configured so as to have an air intake port at a first end and so as to have an exhaust port at a second end. The ion generating device is disposed inside the duct. The mounting plate is configured so as to serve to attach the duct to the housing. The mounting plate has an opening aperture communicating with the duct, and is configured so as to be attachable to the housing and so as to function as a part of the housing when it is attached to the housing.

6 Claims, 8 Drawing Sheets

ION GENERATING UNIT WITH ION GENERATING FUNCTION AND IMAGE FORMING APPARATUS PROVIDED THEREWITH

CROSS REFERENCE

This Nonprovisional application claims priority under 35 U.S.C. §119(a) on Patent Application No. 2009-262987 filed in Japan on Nov. 18, 2009, the entire contents of which are hereby incorporated by reference.

BACKGROUND OF THE INVENTION

The present invention relates to an ion generating unit having an ion generating function and an image forming apparatus provided therewith.

It is no exaggeration to say that an image forming apparatus such as a copier or a printer is an essential device in office; in fact, they are installed in most offices. Besides, in recent years, image forming apparatus are also spreading in ordinary households and hospitals, and have become an article very close to us.

By the way, among the image forming apparatus are known such ones that suck air from surroundings of the image forming apparatus into the interior of its housing, supply the air to its image forming section and fuser section, and then exhaust the air outside the image forming apparatus. Among such image comprising an air cleaning section configured so as to prevent hazardous substances generated inside the apparatus from being emitted outside the apparatus, by removing hazardous substances contained in an air current to be released outside the apparatus and thus cleaning the air current, and then by supplying negative ions (for example, refer to Japanese Patent Unexamined Publication No. 2005-4144 bulletin).

In the technique as described in the above mentioned Japanese Patent Unexamined Publication No. 2005-4144 bulletin, in order to meet the need for removing toner powder, dust, ozone and the like that are occurring with the image forming operation of the image forming section, it is unavoidable to dispose an ion generating section with an electrode in the proximity of the image forming section and in the air current that is formed around the image forming section. As a result, a problem that the efficiency of generating ions of the ion generating section deteriorates at an early stage has occasionally occurred due to an influence of such as silicon and/or the like generated around the image forming section. Accordingly, there has been a problem that the capability to clean the air around the image forming apparatus deteriorates as a period of service of the image forming apparatus gets longer.

On the other hand, in a case where a unit provided with an air cleaning function is disposed at the outside of the image forming apparatus so as to take a large distance between the ion generating section and the image forming section, extra space becomes necessary for installing such a unit; consequently, there arises a problem that the space required for installing such an image forming apparatus increases.

The present invention is directed to providing an image forming apparatus capable of maintaining a function of stable generation of ions for an extended period of time, without increasing the space required for installing an image forming apparatus.

SUMMARY OF THE INVENTION

An ion generating unit according to the present invention is configured so as to be capable of being installed inside a housing of an image forming apparatus. The ion generating unit comprises a duct, an ion generating device, a mounting plate and an air current generating section.

The duct is configured so as to have an air intake port at a first end, and an exhaust port at a second end. The ion generating device is disposed inside the duct.

The mounting plate is configured so as to serve to attach the duct to the housing. The mounting plate has an opening aperture communicating with the duct, and is configured so as to be attachable to the housing, and so as to function as a part of the housing when it is mounted to the housing.

The air current generating section is disposed inside the duct, and is configured such that an air current is generated inside the duct from the first end toward the second end. An example of the air current generating section includes a variety of fans. For example, it is recommended to provide a fan sending the air off from upstream of the ion generating device toward the ion generating device. Otherwise, it is also possible to provide a fan sucking the air from the proximity of the second end. However, because of the nature that a generated ion is prone to annihilate when the ion comes into contact with an object, it may be said that in disposing a fan it is preferred to dispose the fan upstream from the ion generating device.

In this configuration, the ion generating device of the ion generating unit housed inside the image forming apparatus is disposed in the duct. This results in positioning the ion generating device in a space isolated from the space where the image forming section resides in the housing, and thus influence of silicon or the like, which is generated from the image forming section, on the ion generating device is prevented.

Also, because the ion generating unit is disposed utilizing effectively a vacant space left in the interior of the housing, it does not have to occur that the ion generating unit protrudes outside the housing; consequently, even with an ion generating unit installed, the space required for installing the image forming apparatus does not increase.

In the above mentioned configuration, it is preferred that a filter for cleaning the air that is sucked into the duct is further provided at the first end located on a side where air is sucked into the duct. Provided with such a filter, the ion generating device becomes less likely to come into contact with dust; thus, further extension of service life of the ion generating unit becomes to be sought.

According to the present invention, it is enabled to maintain a function of stable generation of ions for an extended period of time, without increasing the space required for installing an image forming apparatus.

DETAILED DESCRIPTION OF THE INVENTION

Figure 1:
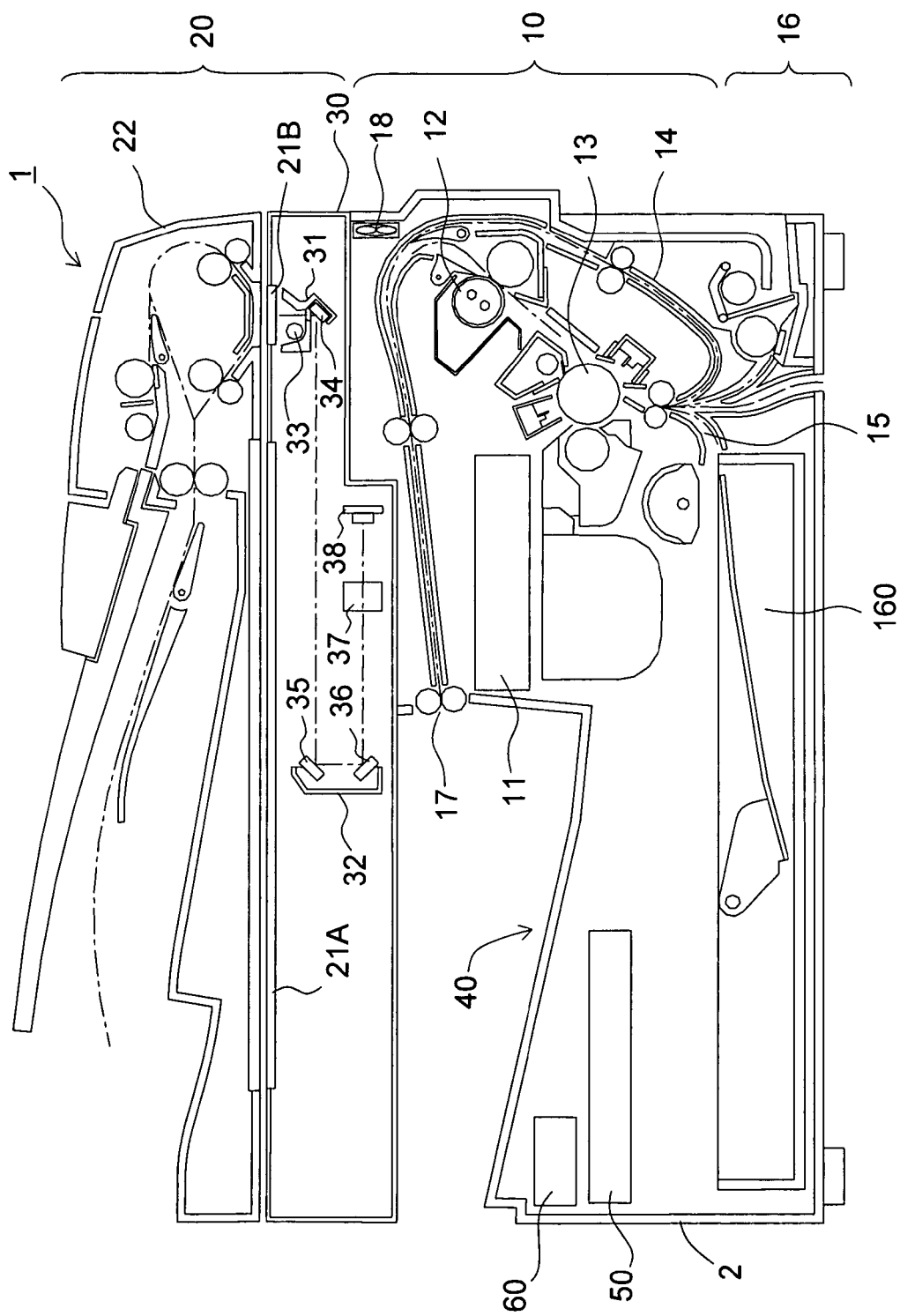
FIG. 1 is a drawing showing an outline of a copier according to an embodiment of the present invention.

FIG. 1 is a drawing showing a configuration of a copier 1 according to an embodiment of the present invention. As shown in the figure above, the copier 1 comprises a document reading section 20, an image forming section 10 and a paper supply section 16. The document reading section 20 comprises document tables 21A, 21B made of a transparent glass each, a scanner unit 30 for reading an image of a document that is placed on the document table 21A or 21B, and an automated document feeder (henceforth referred to as RADF) 22, which is capable of processing a double sided document, for automatically supplying and conveying the document to the document table 21B.

The document table 21A is used when a document is read in a document stationary mode, whereas the document table 21B is used when a document is read in a document feeding mode using the RADF 22. The RADF 22 includes a document tray, and conveys a plurality of documents that are placed on the document tray automatically piece by piece onto the document table 21B. Besides, the RADF 22, so as to have the scanner unit 30 read a single side or both sides of a document depending on a user's choice, comprises a conveying path for a single sided document, a conveying path for a double sided document, a conveying path switching means, a group of sensors or the like to monitor and supervise the state of the document passing each section.

The scanner unit 30 comprises a first scan unit 31, a second scan unit 32, an optical lens 37 and a photoelectric conversion element (henceforth referred to as CCD) 38. The first scan unit 31 is equipped with a lamp reflector assembly 33 to give an exposure of a document face and a first reflecting mirror 34 for leading a reflected light image from the document to the CCD 38. The second scan unit 32 is equipped with a second reflecting mirror 35 and a third reflecting mirror 36 for leading a reflected light image from the first scan unit 31 to the CCD 38. The optical lens 37 forms an image of the reflected light image from the document on the CCD 38. The CCD 38 converts the reflected light image from the document into an electrical image signal.

With the above mentioned configuration of the document reading section 20, an image of the document placed on the document table 21 is formed on the CCD 38 line by line sequentially, and thus the image of the document is read. The image data that have been read by the scanner unit 30, after having been sent to an image processing section which is not illustrated, having undergone a variety of image processing, and once being stored in a memory section provided in the copier 1, are then transferred to the image forming section 10 in response to output instructions.

To the image forming section 10 is formed a paper conveying path between areas from the paper supply section 16 where paper to undergo an image forming process is contained, via an image forming position, to a paper discharge roller 17 that discharges paper to a paper discharge section 40 of an intra-body paper discharge model. Moreover, the image forming section 10 is equipped with a conveyor system along the paper conveying path, a laser writing unit 11, and an electrophotography processing section 13 for forming an image.

The laser writing unit 11 comprises: a semiconductor laser source that emits a laser beam depending on the image data supplied from the above mentioned document reading section 20 or image data transferred from an external instrument such as a personal computer; a polygonal mirror that deflects a laser beam at an equal angular velocity; and a f-θ (theta) lens for making a correction such that the laser beam deflected at the equal angular velocity scans at a uniform rate on the photoconductor drum in the electrophotography processing section 13, and so forth.

The electrophotography processing section 13 comprises, around the photoconductor drum as an image bearing member, an electrifier for charging the photoconductor drum with electricity uniformly, a developing device for supplying a developer to an electrostatic latent image formed on the photoconductor drum by the laser writing unit 11, a transcription device for transcribing onto paper a developer image on the photoconductor drum, a stripper for stripping paper off the photoconductor drum, a cleaning device for removing the developer remaining on the photoconductor drum, and a static eliminator for discharging static electricity from a surface of the photoconductor drum.

Additionally, on the upstream side of the electrophotography processing section 13 in the paper conveying path is disposed a conveying section 15 that conveys paper contained in a paper cassette 160 of the paper supply section 16 to a transcription site located between the photoconductor drum and the transcription device in the electrophotography processing section 13. Also, on the downstream side of the electrophotography processing section 13 in the paper conveying path is disposed a fuser 12 for fixing by heat and pressure a non-fused developer image adhering onto paper. Further, on the downstream side of the fuser 12 is disposed a resupplying path 14 for supplying paper again to form an image again to a rear face of the paper that has undergone a fixing. And, in the proximity of the fuser 12 is disposed an exhaust fan 18 configured so as to discharge gas surrounding the electrophotography processing section 13 and the fuser 12 to outside of the copier 1.

The copier 1 comprises a power supply unit 50 and an ion generating unit 60 above the paper supply section 16 and below the paper discharge section 40. The power supply unit 50 is configured so as to supply electric power to each part of the copier 1.

The ion generating unit 60 is configured so as to ionize water vapor in the air by corona discharge and to generate approximately equal amounts of positive ions and negative ions. In this embodiment, the positive ion is a hydrogen ion ($H^+$) with a plurality of water molecules surrounding thereof, and is represented as $H^+ (H_2O)m$ (m denotes a natural number). On the other hand, the negative ion is an oxygen ion ($O_2^-$) with a plurality of water molecules surrounding thereof, and is represented as $O_2^- (H_2O)n$ (n denotes a natural number). The positive ions and/or negative ions, when they adhere to the surface of a bacterium floating around the copier 1, chemically react and generate hydrogen peroxide $H_2O_2$ as an activated species or a hydroxyl group free radicals .OH.

The hydrogen peroxide $H_2O_2$ or hydroxyl group free radicals .OH, by exhibiting an extremely strong activity, can sterilize bacteria floating in the air.

Figure 2A:
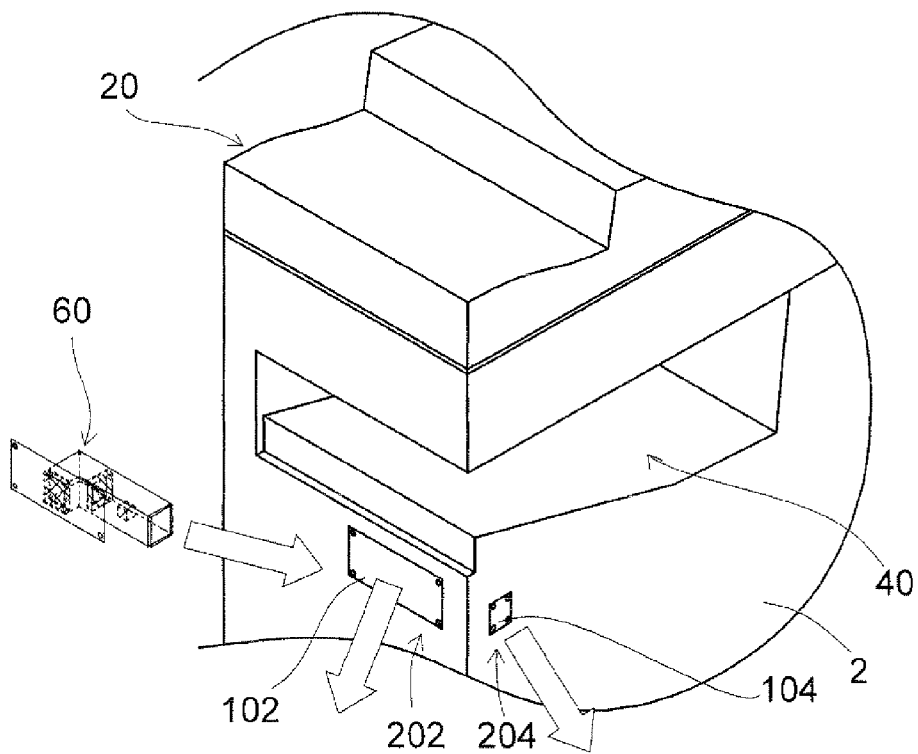
FIG. 2A is a drawing showing a state before an ion generating unit is installed in the copier.

As shown in FIG. 2A, a housing 2 comprises a first opening 202 and a second opening 204 to install the ion generating unit 60. The first opening 202 and the second opening 204 are covered with a cover member 102 and a cover member 104 respectively. Because the cover member 102 and the cover member 104 are screwed to the housing 2, they are detachable from the housing arbitrarily.

Figure 2B:
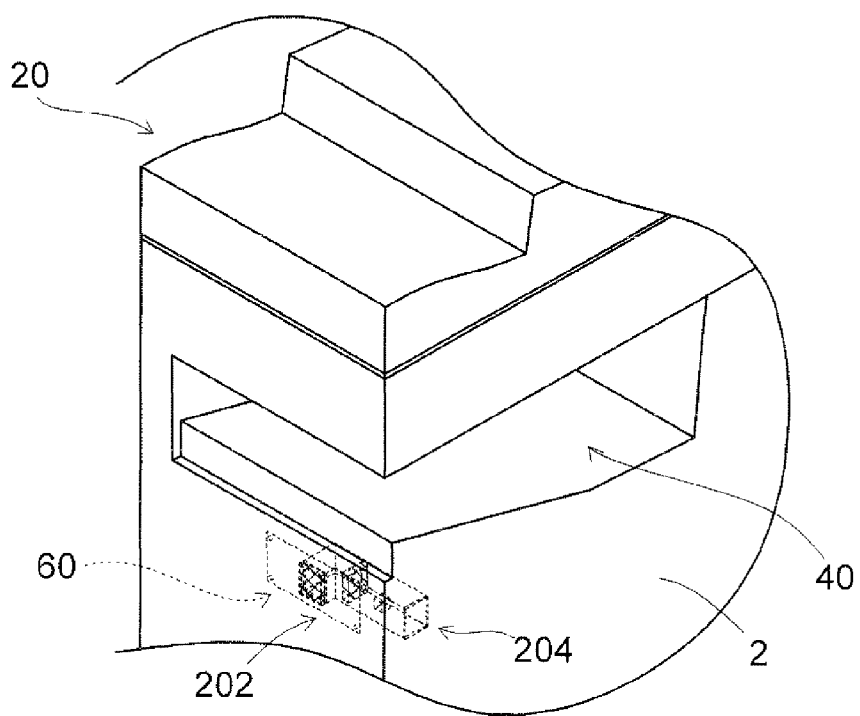
FIG. 2B is a drawing showing a state after the ion generating unit is installed in the copier.

When the ion generating unit 60 is installed inside the copier 1, as shown in FIG. 2A, the cover member 102 and the cover member 104 that are respectively screwed to the side face and the front face of the housing 2 of the copier 1 are first removed. Then, as shown in FIG. 2B, through the first opening 202 the ion generating unit 60 is inserted into the interior of the housing 2 of the copier 1.

Figure 3:
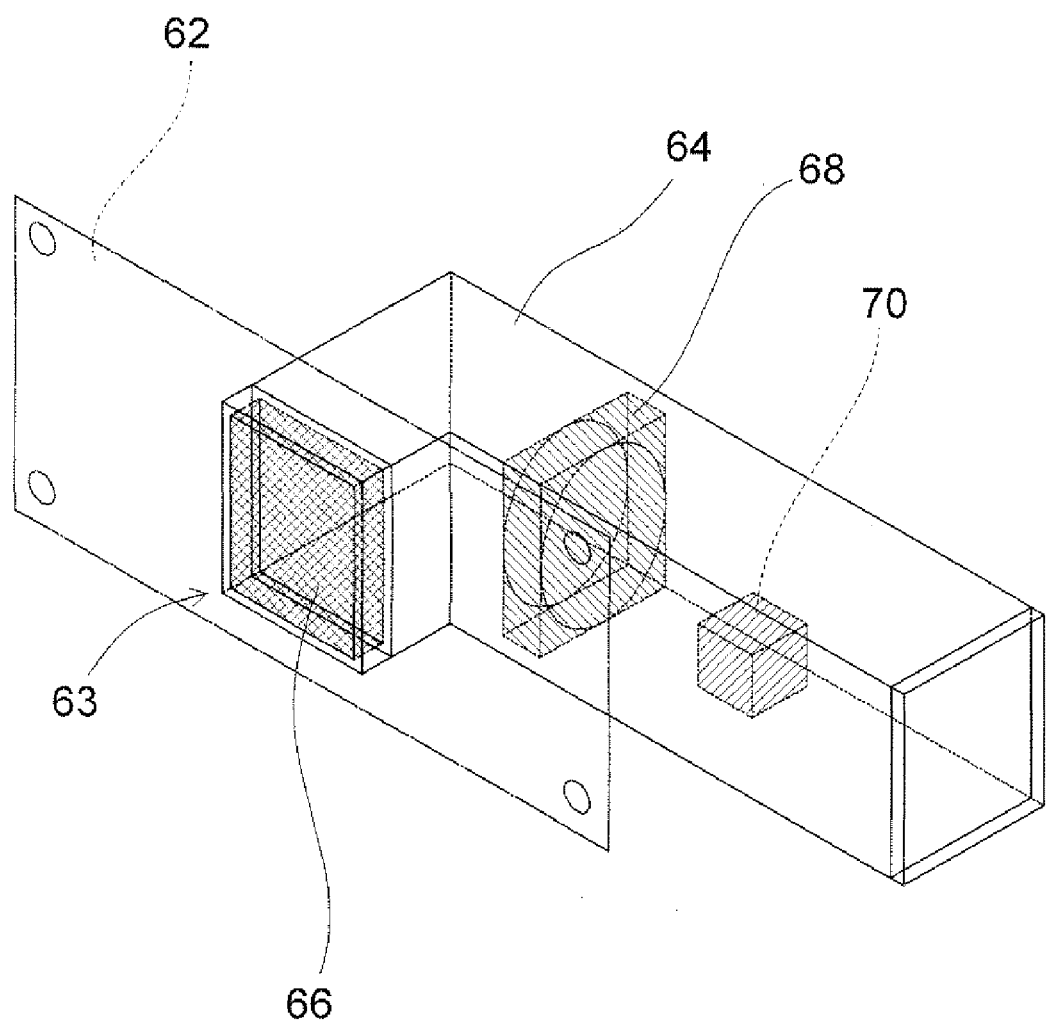
FIG. 3 is a drawing showing an outline of a configuration of the ion generating unit.

As shown in FIG. 3, the ion generating unit 60 comprises a mounting plate 62, a duct 64, a filter 66, a fan 68 and an ion generating device 70. The mounting plate 62 is configured so as to be of the same size same as the cover member 102, and so as to be attachable to the housing 2 of the copier 1 with screws in such a manner as to cover the first opening 202.

The duct 64 is configured so as to define a pathway of air flow, and is connected to the mounting plate 62. To be concrete, an opening aperture 63 corresponding to a cross section of the duct 64 is formed to the mounting plate 62, and the duct 64 is fitted into the opening aperture 63. Although the duct 64 is glued to the mounting plate 62 by an adhesive in this embodiment, it is also possible that the duct 64 is screwed to the mounting plate 62 or likewise so as to be separable from each other.

The filter 66 is installed in the proximity of a first end that is to be an air suction side of the duct 64. The filter 66 is configured so as to capture dirt such as dust, toner, paper powder and the like that are entering into the duct 64. For the filter 66, although employing the one that has a common function of capturing dust is fine as a general rule, adopting the one that has a function of adsorbing silicon is preferred.

The fan 68 is installed between the filter 66 and the ion generating device 70 in the duct 64. The fan 68 is configured so as to generate an air flow in the duct 64 from the first end toward a second end that is to be an air exhaust side.

The ion generating device 70 is configured so as to ionize water vapor on the air inside the duct 64 by corona discharge, and so as to generate approximately equal amounts of positive ions and negative ions. However, configuration of the ion generating device 70 is not limited to that of this embodiment.

Figure 4:
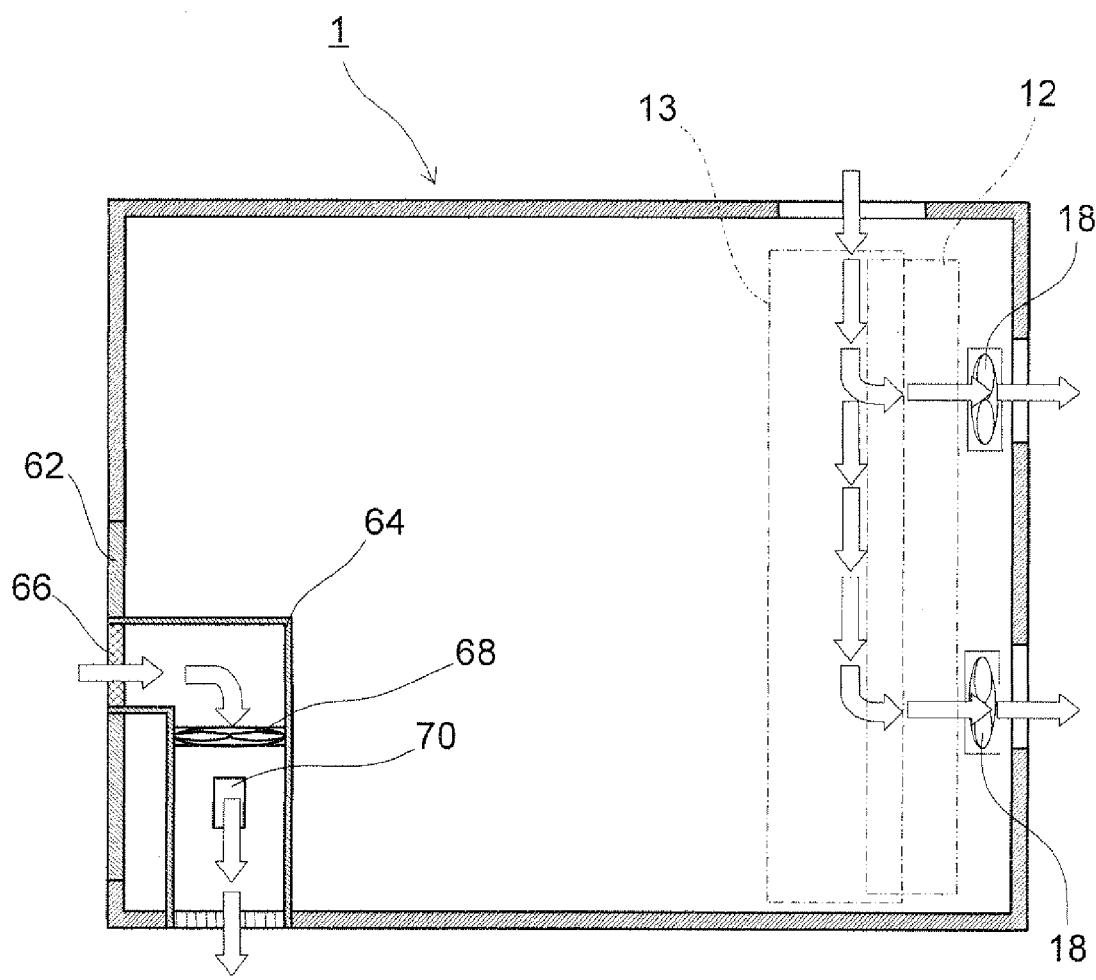
FIG. 4 is a drawing showing a manner in which the ion generating unit is installed in the copier.

In the above-mentioned configuration, the ion generating device 70 is disposed inside the duct 64; and this results in the ion generating device 70 installed in a space that is completely isolated from the air inside the copier 1, as shown in FIG. 4. In particular, because the ion generating device 70 is disposed in such a manner that mixture will not occur with an air current that is produced in the vicinity of the electrophotography processing section 13 and the fuser 12 by suction of an exhaust fan 18, deterioration of efficiency of generating ions of the ion generating device 70 due to damage and/or pollution of corona electrodes or the like will not occur; thus, efficiency of generating ions of the ion generating device 70 is maintained for an extended period of time.

Besides, because an air intake port of the ion generating unit 60 is installed in a face different from the face in which the exhaust fan 18 is installed in the housing of the copier 1, it is prevented from occurring that the air exhausted from the exhaust fan 18 is sucked into the ion generating unit 60.

As a general rule, it is preferred that the ion generating unit 60 is disposed at a position far apart from the electrophotography processing section 13 (in particular, the developing device) and the fuser 12. For example, in a case where the electrophotography processing section 13 and the fuser 12 are located on the right side of the copier 1, it is preferred that the ion generating unit is disposed on the left side of the copier 1.

Further, because the filter 66 for cleaning the air is installed on the air suction side in the duct 64, damage and/or pollution of corona electrodes of the ion generating device 70 is prevented more effectively. Accordingly, it is enabled that efficiency of generating ions of the ion generating device 70 is maintained high over an entire usable period of the copier 1.

Figure 5A:
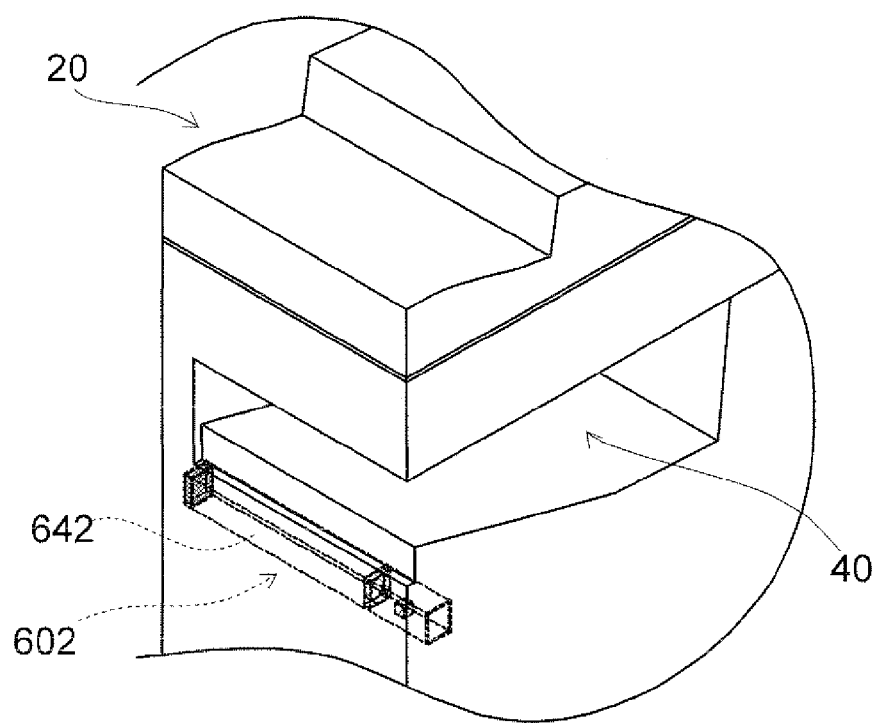
FIG. 5A is a drawing showing a variation of an ion generating unit employing a linear duct extending through the entire length in the direction of the depth of the copier.

Subsequently, using FIG. 5A and FIG. 5B, variations of an ion generating unit are explained. Although the above mentioned ion generating unit 60 uses a L-shaped duct 64 in plane view, it is also possible, as shown in FIG. 5A, to use a linear duct 642 extending through the entire length in the direction of the depth of the copier 1. In installing an ion generating device 602 having such a duct 642, it is recommended, for example, that an air suction port be disposed in the rear face of the housing of the copier 1 and that an air exhaust port be disposed in the front face of the housing. Because there is relatively much room available over the entire length of the direction of the depth of the copier 1 in between the paper supply section 16 and the paper discharge section 40, installing the ion generating device 602 can be fairly easy.

Figure 5B:
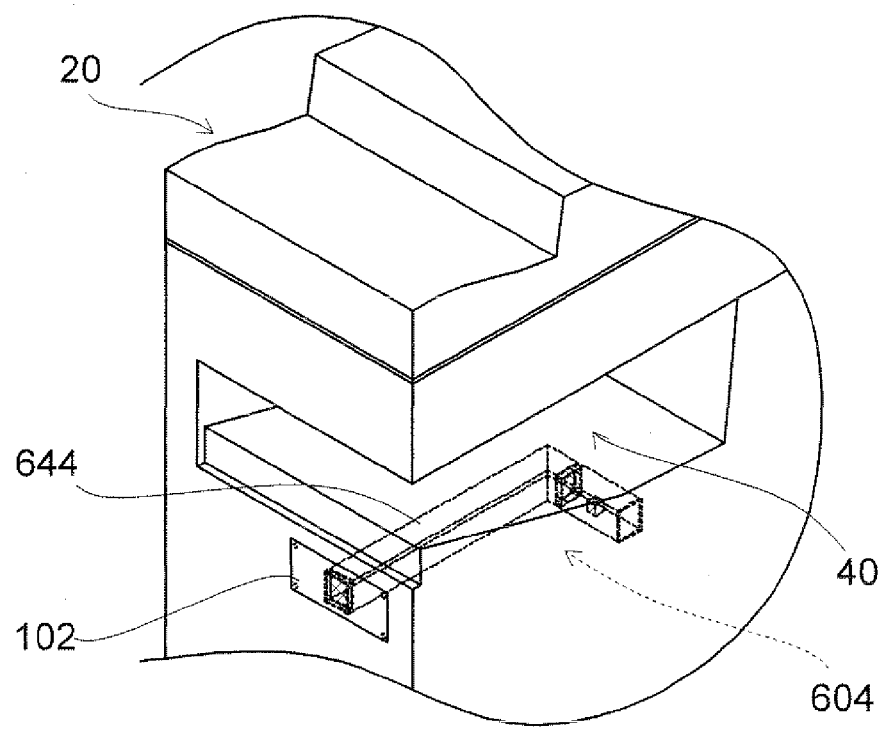
FIG. 5B is a drawing showing another variation of an ion generating unit employing a duct extending long in the direction of the width of the copier.

Additionally, although, in the above mentioned ion generating unit 60, both the air suction port and the air exhaust port are disposed in the proximity of the side face of the housing of the copier 1, it is also possible, as shown in FIG. 5B, to cause to exhaust the air from a position apart from a side face of the housing (for instance, middle of the direction of the width of the copier 1). In this case, it is recommended to use, instead of the ion generating unit 60, an ion generating unit 604 having a duct 644 extending long in the direction of the width of the copier 1.

Figure 6A:
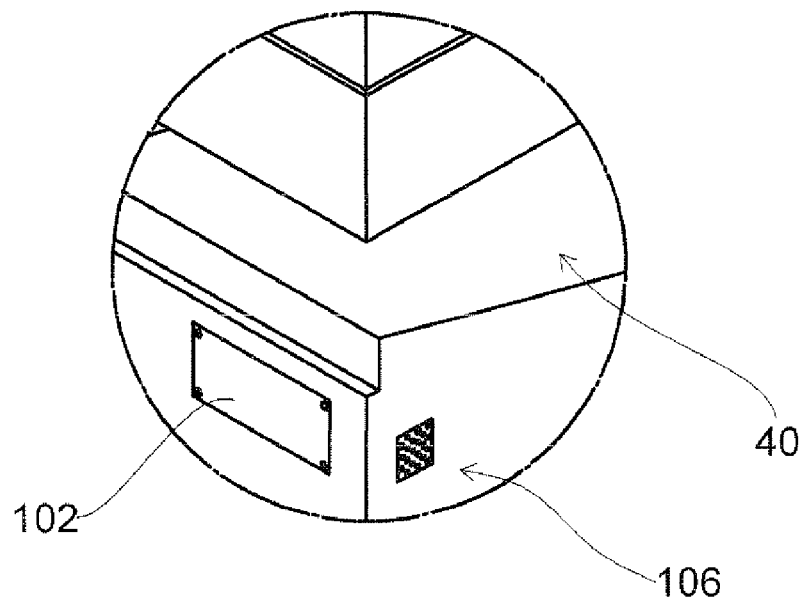
FIG. 6A is a drawing showing a configurative variation of the housing of the copier in which the housing of the copier is provided with a mesh-shaped air vent in advance.

Subsequently, using FIG. 6A and FIG. 6B, configurative variations of an air exhaust port is explained. In securing an air exhaust port of the ion generating units 60, 602, and 604, the cover member 104 was to be removed from the housing; however, as shown in FIG. 6A, the housing of the copier 1 may be provided with a mesh-shaped air vent in advance. Further, as shown in FIG. 6B, the housing of the copier 1 may be provided with a louver in advance.

Figure 6B:
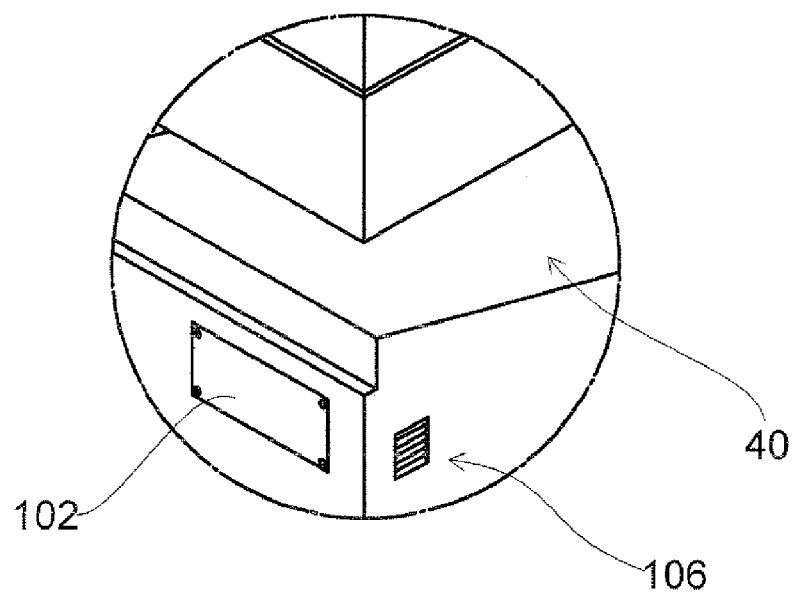
FIG. 6B is a drawing showing another configurative variation of the housing of the copier in which the housing is provided with a louver in advance.

With the configuration as described in FIG. 6A or FIG. 6B, it is not necessary to remove the cover member 104 from the housing when the ion generating unit 60, 602 or 604 is installed. Besides, even when the ion generating unit 60, 602 or 604 is not installed, visual appearance of the copier 1 is not spoiled.

Moreover, although, in the above mentioned embodiments, intake and exhaust of the air to and from the ion generating unit are performed respectively in separate faces of the housing, it is also possible to perform intake and exhaust of the air to and from the ion generating unit in an identical face of the housing.

Figure 7:
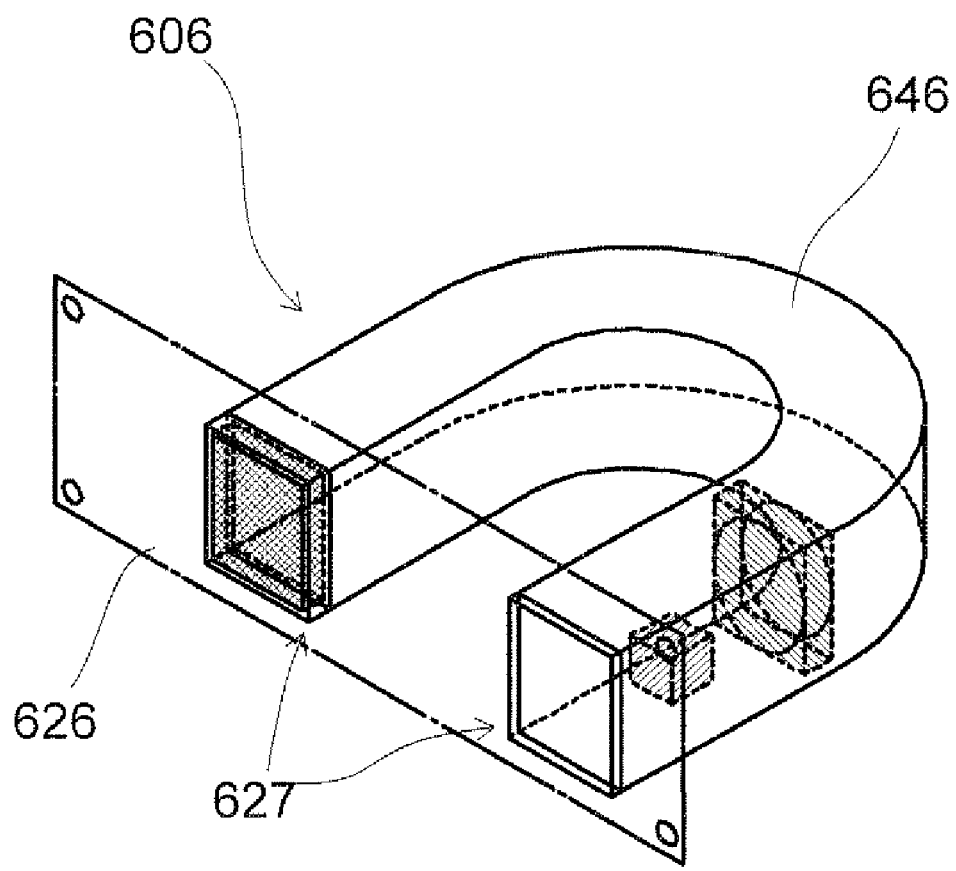
FIG. 7 is a drawing showing a variation of an ion generating unit.

For example, as shown in FIG. 7, an ion generating unit 606 having a U-shaped duct 646 in plane view may be used. In this case, it is preferred that the ion generating unit 606 is provided with a mounting plate 626 on which two opening apertures 627 are formed of a size corresponding to a cross section of the duct 646. With such a configuration, installing the ion generating unit 606 to the copier 1 becomes easier.

Although, in the above mentioned embodiments, cross-sections of the ducts 64, 642, 644 and 646 are of a rectangular form, cross-section of the duct may be of a circular form, or of other geometries.

Figure 8A:
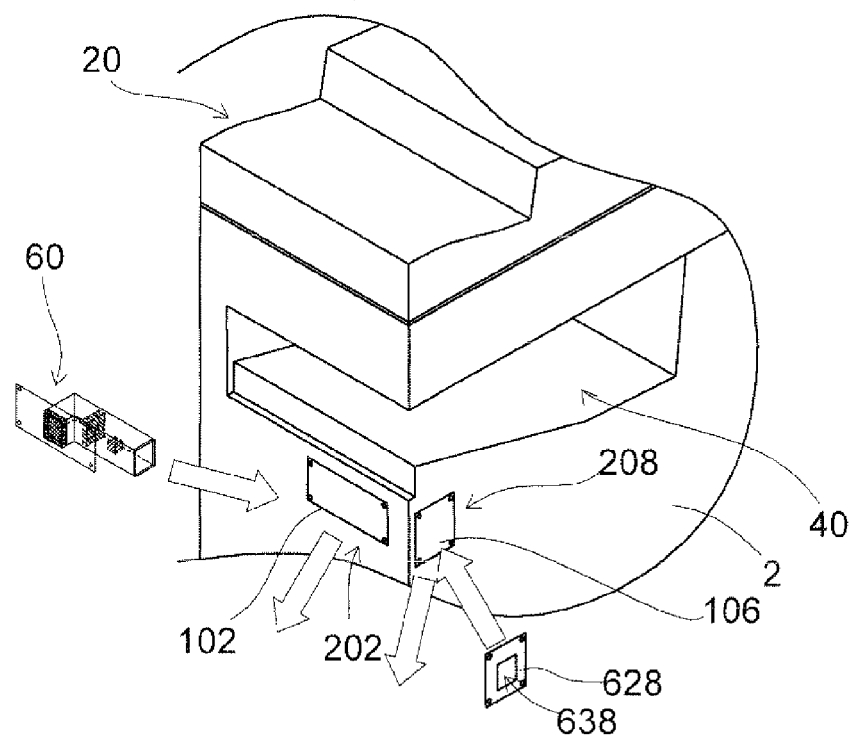
FIG. 8A is a drawing showing a state before an ion generating unit is installed in an image forming apparatus according to another embodiment of the present invention.
Figure 8B:
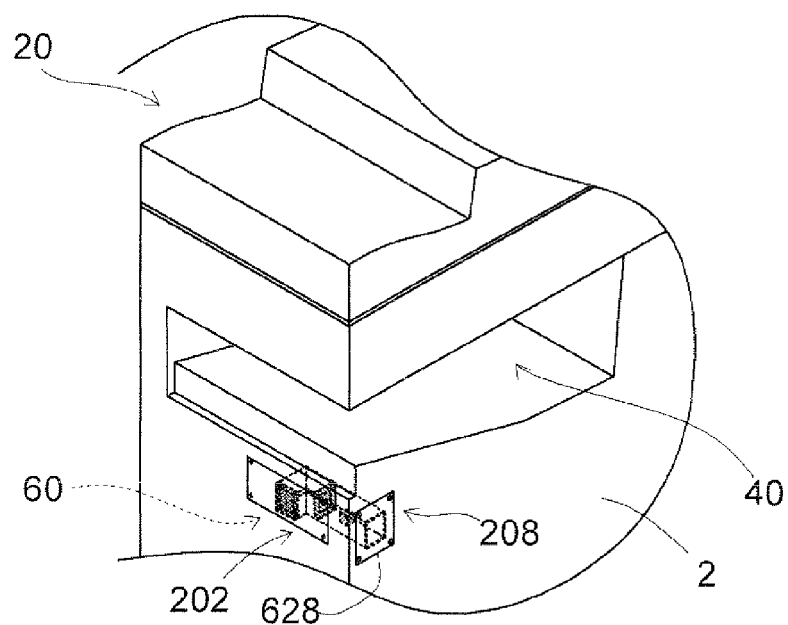
FIG. 8B is a drawing showing a state after the ion generating unit is installed in the image forming apparatus according to the other embodiment.

Further, although, in the above mentioned embodiments, examples were explained in which the duct 64, 642, 644 or 646 was attached to the housing 2 using a single mounting plate 62, it is also possible to use a plurality of mounting plates. For example, as shown in FIG. 8A and FIG. 8B, it is recommended to use a mounting plate 628 that has an opening aperture 638 communicating with the second end of the duct 64 and is configured so as to be attachable to the housing 2, together with the above mentioned mounting plate 62. In this case, a third opening 208 that is greater than the above mentioned second opening 204 is provided to the housing 2.

The above explanation of the embodiments is nothing more than illustrative in any respect, nor should be thought of as restrictive. Scope of the present invention is indicated by claims rather than the above embodiments. Further, it is intended that all changes that are equivalent to a claim in the sense and realm of the doctrine of equivalence be included within the scope of the present invention.

What is claimed is:

1. An ion generating unit capable of being installed inside a housing of an image forming apparatus, the unit comprising:
    a duct having an air intake port at a first end for receiving air from an exterior of said housing of said image forming apparatus and an exhaust port at a second end for expelling air from inside said duct to a region exterior of said housing of said image forming apparatus;
    an ion generating device disposed inside said duct;
    a mounting plate for attaching said duct to said housing, wherein the mounting plate has an opening aperture communicating with said duct, and is configured so as to be attachable to said housing and so as to function as a part of said housing when attached to said housing; and
    an air current generating section disposed inside said duct and configured so as to generate an air current inside said duct from said first end toward said second end to expel air from inside said duct that has been treated by said ion generating device to the exterior of said housing, wherein the inside of said duct is not in communication with air inside the housing of the image forming apparatus.

2. The ion generating unit as claimed in claim 1, wherein a filter for cleaning the air that is sucked into said duct is provided at the first end of said duct.

3. An image forming apparatus provided with an ion generating unit as claimed in claim 1, the apparatus comprising:
    a housing having a first opening formed at a position corresponding to the air intake port of said duct and a second opening formed at a position corresponding to the exhaust port of said duct; and
    an image forming section disposed inside said housing and configured so as to perform an image forming process based on image data supplied.

4. The image forming apparatus as claimed in claim 3, wherein said first opening of said housing is disposed in a face different from a face of an exhaust port for said image forming section in said housing.

5. The image forming apparatus as claimed in claim 3, wherein said image forming section is disposed at a first side edge section in said housing, and said ion generating unit is disposed at a second side edge section located opposite said first side edge section.

6. The image forming apparatus as claimed in claim 4, wherein said image forming section is disposed at a first side edge section in said housing, and said ion generating unit is disposed at a second side edge section located opposite said first side edge section.

* * * * *